(12) United States Patent
Rami et al.

(10) Patent No.: US 8,063,078 B2
(45) Date of Patent: Nov. 22, 2011

(54) UREA-COMPOUNDS ACTIVE AS VANILLOID RECEPTOR ANTAGONISTS FOR THE TREATMENT OF PAIN

(75) Inventors: Harshad Kantilal Rami, Harlow (GB); Mervyn Thompson, Harlow (GB)

(73) Assignee: GlaxoSmithKline LLC, Philadelphia, PA (US)

( * ) Notice: Subject to any disclaimer, the term of this patent is extended or adjusted under 35 U.S.C. 154(b) by 1362 days.

(21) Appl. No.: 10/489,277

(22) PCT Filed: Sep. 13, 2002

(86) PCT No.: PCT/GB02/04206
§ 371 (c)(1),
(2), (4) Date: Aug. 11, 2007

(87) PCT Pub. No.: WO03/022809
PCT Pub. Date: Mar. 20, 2003

(65) Prior Publication Data
US 2009/0163506 A1    Jun. 25, 2009

(30) Foreign Application Priority Data

Sep. 13, 2001 (GB) .................................. 0122156.3
Dec. 20, 2001 (GB) .................................. 0130503.6
Dec. 20, 2001 (GB) .................................. 0130505.1
Dec. 20, 2001 (GB) .................................. 0130547.3

(51) Int. Cl.
*A61K 31/4025* (2006.01)
*A61K 31/443* (2006.01)
*C07D 207/44* (2006.01)
*C07D 401/04* (2006.01)

(52) U.S. Cl. ..................... 514/343; 514/422; 546/276.4; 546/279.1; 548/518

(58) Field of Classification Search .................. 514/343, 514/422; 548/518; 546/276.4, 279.1
See application file for complete search history.

(56) References Cited

U.S. PATENT DOCUMENTS

| | | | |
|---|---|---|---|
| 3,424,760 A | 1/1969 | Welstead et al. | |
| 3,424,761 A | 1/1969 | Lunsford et al. | |
| 4,001,422 A | 1/1977 | Danilewicz et al. | |
| 7,220,856 B2 * | 5/2007 | Dunning et al. | 540/484 |

FOREIGN PATENT DOCUMENTS

| | | |
|---|---|---|
| EP | 0401903 | 12/1990 |
| EP | 0347000 | 10/1994 |
| EP | 0790240 | 8/1997 |
| EP | 1392651 | 3/2004 |
| GB | 2226313 | 6/1990 |
| JP | 2000080085 | 3/2000 |
| JP | 20020880073 | 3/2002 |
| JP | 2004527571 | 9/2004 |
| WO | 9209285 | 6/1992 |
| WO | 9219618 | 11/1992 |
| WO | 9900121 | 1/1999 |
| WO | 9900128 | 1/1999 |
| WO | 0050387 | 8/2000 |
| WO | 0055139 | 9/2000 |
| WO | 0128987 | 4/2001 |
| WO | 0208221 | 1/2002 |
| WO | 0216317 | 2/2002 |
| WO | 0216318 | 2/2002 |
| WO | 0216319 | 2/2002 |
| WO | 02090326 | 11/2002 |
| WO | 03022809 | 3/2003 |
| WO | WO 2004/024710 | 3/2004 |
| WO | 2004056394 A1 | 7/2004 |
| WO | 2005103018 A1 | 11/2005 |

OTHER PUBLICATIONS

10489277_STN preliminary_02142010.*
U.S. Appl. No. 60/451,687.*
Vippagunta et al., Advanced Drug Delivery Reviews, vol. 48, p. 3-26.*
Pi-Chi Pan, Chung-Ming Sun; Soluble Polymer-Supported Synthesis of Arylpiperazines; Tetrahedron Letters; 1998; 39 No. 51 1998; 9505-9508; .
Masters, J. J et al; Non-Amidine-Containing 1,2-Dibenzamidobenzene Inhibitors of Human Factor Xa with Potent Anticoagulant and Antithrombotic Activity; Journal of Medicinal Chemistry; 2000; 43 (11); 2087-2092.
Taniguchi, Nobuaki et al; Preparation of heteroyclic moiety-containing benzonitrile derivatives a antiangrogen agents; Database Caplus online; Mar. 26, 2002; 136; 279475; Chemical Abstracts Service; Columbis, Ohio, US.
Hacksell, U et al; 3-Phenylpiperidines. Central dopamine-autoreceptor stimulating activity; Journal of Medicinal Chemistry; 1981; 24; 1475-1482.
Le Bars D et al; Animal models of Nociception; Pharmacological Reviews; 2001; 53; 597-652.
March et al; Advanced Organic Chemistry; 1992; 4; 1216-1218.
March et al; Advanced Organic Chemistry; 1992; 4; 417.
Hassan, J et al; Aryl-aryl bond formation one century after the discovery of the Ullmann reaction.; Chem Rev; 2002; 102; 1359-1469.
Helsley G. C. et.al.; Synthesis and Biological Activity of some 1-substitutes 3-pyrrolidinylureas; Journal of Medicinal Chemistry; 1968; 11 (5); 1034-1037; Am. Chem. Soc.; Washington, US.
Gamage Sa et al; Structure-activity relationships for pyrido-, imidazo-, pyrazolo-, pyrazino-, and pyrrolophenazinecarboxamides as topoisomerase-targeted anticancer agents.; Journal of Medicinal Chemistry; 2002; 45; 740-743.

(Continued)

*Primary Examiner* — Yong Chu
(74) *Attorney, Agent, or Firm* — Robert H. Brink

(57) ABSTRACT

Certain compounds of formula (I),

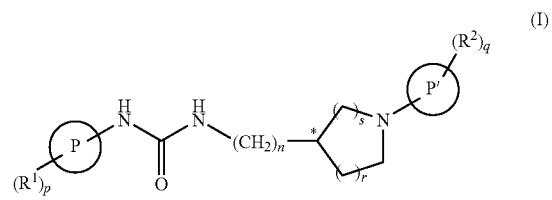

or a pharmaceutically acceptable salt thereof, or a solvate thereof, wherein $R^1$, $R_2$, P, P', n, p, q, r and s are as defined in the specification, a process for preparing such compounds, a pharmaceutical composition comprising such compounds and the use of such compounds and composition in medicine.

3 Claims, No Drawings

OTHER PUBLICATIONS

Smart, D et al; The endogenous lipid anandamide is a full agaonist at the human vanilloid receptor (hVR1).; British Journal of Pharmacology; 2000; 129; 227-230.

March et al; Advanced Organic Chemistry; 1992; 4; 1212.

March et al; Advanced Organic Chemistry; 1992; 4; 378-383.

Berge S M et al; Pharmaceutical Salts; Journal of Pharmaceutical Sciences; 1977; 66, 1; 1-19.

Vorbruggen H.; Advances in Animation of Nitrogen Heterocycles; Advances in Heterocyclic Chemistry; 1990; 49; 117.

Langer M et al; Novel Peptide conjugates for tumor-specific chemotherapy; Journal of Medicinal Chemistry; 2001; 44, 9; 1341-1348.

Graf E et al; Synthesis of 6-Phenyl substituted 2-formylnicotinates.; Synthesis; 1999; 7; 1216-1222.

March et al; Advanced Organic Chemistry; 1992; 4; 419-421.

Szallasi, A., et al.; Vanilloid (Capsaicin) Receptors and Mechanisms; Pharmacological Reviews by the American Society for Pharmacology and Experimental Therapeutics; 1999; 51(2); 159-211.

Freer, R., et al.; Synthesis of Symmetrical and Unsymmetrical Ureas Using Unsymmetrical Diaryl Carbonates; Synthetic Communications; 1996; 26(2); 331-349.

Alonso, D.A., et al.; Lithiated B-Aminoalkyl Sulfones As Mono and Dinucleophiles in the Preparation of Nitrogen Heterocycles: Application to the Synthesis of Capsazepine; Tetrahedron Letters; 1997; 53(13); 4791-4814.

Janusz, J.M., et al.; Vanilloids. 1. Analogs of Capsaicin With Antinociceptive and Antiinflammatory Activity; Journal of Medicinal Chemistry; 1993; 36(18); 2595-2604.

Carr, G E, et al; Sodium Perfluoroalkane Carbgoxylates as Sources of Perfluoroalkyl Groups; Journal of Chem. Soc Perkin Trans 1; 1988; 921-926.

Haga, T, et al; Some New 2-substituted 5-trifluoromethylpyridines; Hetercycles (J for Reviews and Communications in Heter ocyclic Chemistry); 1984; 22 (1); 117-124.

Chizh et al.; The effects of the TRPV1 antagonist Sb-705498 on TRPV1 receptor-mediated activity and inflammatory hyperalgesia in humans; Pain; Oct. 3 2007; 132(1-2); 132-141.

Gunthorpe, M.J. et al.; Characterization of Sb-705498, a potent and selective vanilloid receptor-1 (VR1/TRPV1) antagonist that inhibits the capsaicin-, acid-, and heat-mediated activation of the receptor.; Journal of Pharmacology and Experimental Therapeutics; 2007; 321(3); 1183-1192.

Alenmyr L., et al.; TRPV1-mediated itch in seasonal allergic rhinitis.; Allergy: European Journal of Allergy and Clinical Immunology; May 5 2009; 64(5); 807-810.

Sanchez, Joseph P et. al.; Quinolone Antibacterial AGents. Synthesis and Structure-Activity Relationships of a Series of Amino Acid Prodrugs of Racemic and Chiral 7-(3-Amino-1-pyrrolidinyl)quinolones. Highly Soluble Quinolone Prodrugs with inVivo Pseudomonas Activity; Journal of Medicinal Chemistry; 1992; 35; 1764-1773; Am. Chem. Soc.; Washington, US.

Pope, B M; DI-tert-Butyl dicardbonate; Organic Synthesis; 1978; 57; 45; .

Sinha, Birandra K, et al; Synthesis and Antitumor Properties of Bis(Quinaldine) Derivatives; Journal of Medicinal Chemistry; 1977; 20; 1528; Am. Chem. Soc.; Washington, US.

Sato, T et al; A convenient synthetic method of 1, 3-disubstituted isoquinolines using silver trifluoromethanesulfonate as a key reagent; Chemical Letters; 1983; 791-794; The Chemical Society of Japan.

Greene, T W; Protective groups in organic synthesis; Wiley Book; 1981; Wiley.

* cited by examiner

UREA-COMPOUNDS ACTIVE AS VANILLOID RECEPTOR ANTAGONISTS FOR THE TREATMENT OF PAIN

This is a 371 of International Patent Application No. PCT/GB02/04206, filed 13 Sep. 2002.

This invention relates to novel compounds, especially urea derivatives, having pharmacological activity, processes for their preparation, to compositions containing them and to their use in medicine, especially in the treatment of various disorders.

Vanilloids are a class of natural and synthetic compounds that are characterised by the presence of a vanillyl (4-hydroxy 3-methoxybenzyl) group or a functionally equivalent group. Vanilloid Receptor (VR-1), whose function is modulated by such compounds, has been widely studied and is extensively reviewed by Szallasi and Blumberg (The American Society for Pharmacology and Experimental Therapeutics, 1999, Vol. 51, No. 2.).

A wide variety of Vanilloid compounds of different structures are known in the art, for example those disclosed in European Patent Application Numbers, EP 0 347 000 and EP 0 401 903, UK Patent Application Number GB 2226313 and International Patent Application, Publication Number WO 92/09285. Particularly notable examples of vanilloid compounds or vanilloid receptor modulators are capsaicin or trans 8-methyl-N-vanillyl-6-nonenamide which is isolated from the pepper plant, capsazepine (*Tetrahedron,* 53, 1997, 4791) and olvanil or -N-(4-hydroxy-3-methoxybenzyl)oleamide (*J. Med. Chem.,* 36, 1993, 2595).

U.S. Pat. No. 3,424,760 and U.S. Pat. No. 3,424,761 both describe a series of 3-Ureidopyrrolidines that are said to exhibit analgesic, central nervous system, and pyschopharmacologic activities. These patents specifically disclose the compounds 1-(1-phenyl-3-pyrrolidinyl)-3-phenyl urea and 1-(1-phenyl-3-pyrrolidinyl)-3-(4-methoxyphenyl)urea respectively.

International Patent Applications, Publication Numbers WO 02/08221, WO 02/16317, WO 02/16318 and WO 02/16319 each disclose certain vanilloid receptor antagonists and their use in the treatment of diseases associated with the activity of the vanilloid receptor.

Co-pending International Patent Application Number PCT/EP02/04802 discloses a series of urea derivatives and their use in the treatment of diseases associated with the activity of the vanilloid receptor.

According to a first aspect of the present invention, there is provided a compound of formula (I),

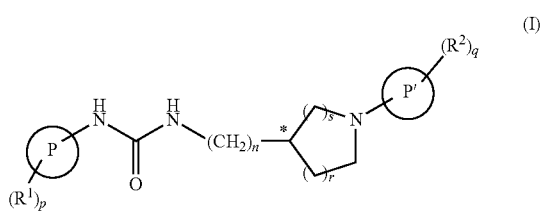

(I)

or a pharmaceutically acceptable salt thereof, or a solvate thereof, wherein:
P and P' are independently selected from aryl and heteroaryl;
$R^1$ and $R^2$ are independently selected from —H, halo, alkyl, alkoxy, cycloalkyl, aralkyl, aralkoxy, cycloalkylalkyl, cycloalkylalkoxy, —CN, —NO$_2$, —OH, —OCF$_3$, —CF$_3$, —NR$^4$R$^5$, —S(O)$_m$R$^6$, —S(O)$_2$NR$^4$R$^5$, —OS(O)$_2$R$^6$, —OS(O)$_2$CF$_3$, —O(CH$_2$)$_x$NR$^4$R$^5$, —C(O)CF$_3$, —C(O)alkyl, —C(O)cycloalkyl, —C(O)aralkyl, —C(O)Ar, —C(O)(CH$_2$)$_x$ OR$^6$, —C(O)(CH$_2$)$_x$NR$^4$R$^5$, —C(O)alkoxy, —C(O)NR$^4$R$^5$, —(CH$_2$)$_x$C(O)alkoxy, —(CH$_2$)$_x$OC(O)R$^6$, —(CH$_2$)$_x$ OR$^6$, —(CH$_2$)$_x$R$^4$R$^5$, —(CH$_2$)$_x$C(O)NR$^4$R$^5$, —(CH$_2$)$_x$N(R$^4$) C(O)R$^6$, —(CH$_2$)$_x$S(O)$_2$NR$^4$R$^5$, —(CH$_2$)$_x$N(R$^4$)S(O)$_2$R$^6$, —ZAr, —(CH$_2$)$_x$S(O)$_2$R$^6$, —(OCH$_2$)$_x$S(O)$_2$R$^6$, —N(R$^4$)S (O)$_2$R$^6$, —N(R$^4$)C(O)R$^6$, —(CH$_2$)$_x$N(R$^4$)S(O)$_2$R$^6$, —(CH$_2$)$_x$ N(R$^4$)C(O)R$^6$ or —(CH$_2$)$_x$C(O)alkyl;

$R^4$ and $R^5$ may be the same or different and represent H or alkyl or $R^4$ and $R^5$ together with the atoms to which they are attached form a $C_{5-8}$azacycloalkane, $C_{3-6}$(2-oxo)azacycloalkane ring or $C_{5-8}$ polymethylene chain optionally interrupted by heteroatoms such as O or —NR$^7$.

Z is O, S or NR$^7$;
$R^6$ is alkyl or aryl;
$R^7$ is hydrogen, alkyl or aryl;
m is 1 or 2;
n is 0, 1, 2 or 3;
p and q are independently 0, 1, 2, 3 or 4;
r is 1, 2 or 3;
s is 0, 1 or 2; and
x is 0, 1, 2, 3, 4, 5 or 6;
with the proviso that said compound of formula (I) is not a compound selected from:

1-(1-phenyl-3-pyrrolidinyl)-3-phenyl urea;
1-(1-phenyl-3-pyrrolidinyl)-3-(4-methoxyphenyl)urea;
N-(4-Fluorophenyl)-N'-[(R)-1-((3-methylphenyl)pyrrolidin-2-ylmethyl)]urea;
N-(2-Bromophenyl)-N'-[((R)-1-(3-methylphenyl)pyrrolidin-3-yl)]urea;
N-(2-Bromophenyl)-N'-[((R)-1-(3-methylphenyl)pyrrolidin-2-ylmethyl)]urea;
N-(4-Fluorophenyl)-N'-[((S)-1-(3-methylphenyl)pyrrolidin-2-ylmethyl)]urea;
N-(2-Bromophenyl)-N'-[((S)-1-(3-methylphenyl)pyrrolidin-2-ylmethyl)]urea;
N-(4-Fluorophenyl)-N'-[((S)-1-(3-methylphenyl)pyrrolidin-3-yl)]urea;
N-(2-Bromophenyl)-N'-[((S)-1-(3-methylphenyl)pyrrolidin-3-yl)]urea;
N-(4-Fluorophenyl)-N'-[((R)-1-(3-methylphenyl)pyrrolidin-3-yl)]urea;
N-(4-Fluorophenyl)-N'-[((R)-1-(3-fluorophenyl)]pyrrolidin-3-yl)]urea;
N-(2-Bromophenyl)-N'-[((R)-1-(3-fluorophenyl)pyrrolidin-3-yl)]urea;
N-(1-Naphthyl)-N'-[((R)-1-(3-methylphenyl)pyrrolidin-3-yl)]urea;
N-(2,3-Dichlorophenyl)-N'-[((R)-1-(3-methylphenyl)pyrrolidin-3-yl)]urea;
N-(2-Bromophenyl)-N'-[((S)-1-(3-fluorophenyl)pyrrolidin-3-yl)]urea;
N-(2-Bromophenyl)-N'-[((R)-1-(4-fluoro-3-methylphenyl) pyrrolidin-3-yl)]urea;
N-(2-Bromophenyl)-N'[((R)-1-(3,4-difluorophenyl)pyrrolidin-3-yl)]urea;
N-(2-Bromophenyl)-N'-[((R)-1-(3-fluoro-4-methylphenyl) pyrrolidin-3-yl)]urea;
N-(3-Chloro-2-methylphenyl)-N'-[((R)-1-(3-methylphenyl) pyrrolidin-3-yl)]urea;
N-(2,3-Dichlorophenyl)-N'-[((R)-1-(3-methylphenyl)pyrrolidin-3-yl)]urea;
N-(2,5-Dichlorophenyl)-N'-[((R)-1-(3-methylphenyl)pyrrolidin-3-yl)]urea;
N-(2,3-Dichlorophenyl)-N'-[((R)-1-(3-fluorophenyl)pyrrolidin-3-yl)]urea;

N-(2,5-Dichlorophenyl)-N'-[((R)-1-(3-fluorophenyl)pyrrolidin-3-yl)]urea;
N-(3-Chloro-2-methylphenyl)-N'-[((R)-1-(3-fluorophenyl)pyrrolidin-3-yl)]urea;
N-(3-Chloro-2-methylphenyl)-N'-[((R)-1-(3,4-difluorophenyl)pyrrolidin-3-yl)]urea;
N-(2,3-Dichlorophenyl)-N'-[((R)-1-(3,4-difluorophenyl)pyrrolidin-3-yl)]urea;
N-(2,5-Dichlorophenyl)-N'-[((R>1-(3,4-difluorophenyl)pyrrolidin-3-yl)]urea;
N-(3-Chloro-2-methylphenyl)-N'-[((R)-1-(3-fluoro-4-methylphenyl)pyrrolidin-3-yl)]urea; and
N-(2,3-Dichlorophenyl)-N'-[((R)-1-(3-fluoro-4-methylphenyl)pyrrolidin-3-yl)]urea.

Suitably, P and P' are independently selected from phenyl and heteroaryl.

In a preferred aspect of the present invention there is provided a subset of compounds of formula (I), of formula (IA),

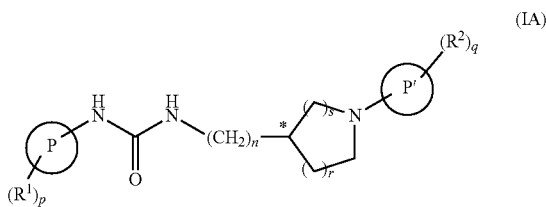

(IA)

or a pharmaceutically acceptable salt thereof, or a solvate thereof, wherein:
P is phenyl, naphthyl, quinolinyl or isoquinolinyl;
P' is phenyl or pyridyl;
$R^1$ and $R^2$ are independently selected from —H, halo, alkyl, alkoxy, cycloalkyl, aralkyl, aralkoxy, cycloalkylalkyl, cycloalkylalkoxy, —CN, —NO$_2$, —OH, —OCF$_3$, —CF$_3$, —NR$^4$R$^5$, —S(O)$_m$R$^6$, —S(O)$_2$NR$^4$R$^5$, —OS(O)$_2$R$^6$, —OS(O)$_2$CF$_3$, —O(CH$_2$)$_x$NR$^4$R$^5$, —C(O)CF$_3$, —C(O)alkyl, —C(O)cycloalkyl, —C(O)aralkyl, —C(O)Ar, —C(O)(CH$_2$)$_x$OR$^6$, —C(O)(CH$_2$)$_x$NR$^4$R$^5$, —C(O)alkoxy, —C(O)NR$^4$R$^5$, —(CH$_2$)$_x$C(O)alkoxy, —(CH$_2$)$_x$OC(O)R$^6$, —(CH$_2$)$_x$OR$^6$, —(CH$_2$)$_x$R$^4$R$^5$, —(CH$_2$)$_x$C(O)NR$^4$R$^5$, —(CH$_2$)$_x$N(R$^4$)C(O)R$^6$, —(CH$_2$)$_x$S(O)$_2$NR$^4$R$^5$, —(CH$_2$)$_x$N(R$^4$)S(O)$_2$R$^6$, —ZAr, —(CH$_2$)$_x$S(O)$_2$R$^6$, —(OCH$_2$)$_x$S(O)$_2$R$^6$, —N(R$^4$)S(O)$_2$R$^6$, —N(R$^4$)C(O)R$^6$, —(CH$_2$)$_x$N(R$^4$)S(O)$_2$R$^6$, —(CH$_2$)$_x$N(R$^4$)C(O)R$^6$ or —CH$_2$)$_x$C(O)alkyl;
$R^4$ and $R^5$ may be the same or different and represent H or alkyl or $R^4$ and $R^5$ together with the atoms to which they are attached form a $C_{3-6}$azacycloalkane, $C_{3-6}$(2-oxo)azacycloalkane ring or $C_{5-8}$ polymethylene chain optionally interrupted by heteroatoms such as 0 or —NR$^7$.
Z is O, S or NR$^7$;
$R^6$ is alkyl or aryl;
$R^7$ is hydrogen, alkyl or aryl;
m is 1 or 2;
n is 0, 1, 2 or 3;
p and q are independently 0, 1, 2, 3 or 4;
r is 1, 2 or 3;
s is 0, 1 or 2; and
x is 0, 1, 2, 3, 4, 5 or 6;
with the proviso that said compound of formula (IA) is not a compound selected from:
1-(1-phenyl-3-pyrrolidinyl)-3-phenyl urea;
1-(1-phenyl-3-pyrrolidinyl)-3-(4-methoxyphenyl)urea;
N-(4-Fluorophenyl)-N'-[(R)-1-((3-methylphenyl)pyrrolidin-2-ylmethyl)]urea;

N-(2-Bromophenyl)-N'-[((R)-1-(3-methylphenyl)pyrrolidin-3-yl)]urea;
N-(2-Bromophenyl)-N'-[((R)-1-(3-methylphenyl)pyrrolidin-2-ylmethyl)]urea;
N-(4-Fluorophenyl)-N'-[((S)-1-(3-methylphenyl)pyrrolidin-2-ylmethyl)]urea;
N-(2-Bromophenyl)-N'-[((S)-1-(3-methylphenyl)pyrrolidin-2-ylmethyl)]urea;
N-(4-Fluorophenyl)-N'-[((S)-1-(3-methylphenyl)pyrrolidin-3-yl)]urea;
N-(2-Bromophenyl)-N'-[((S)-1-(3-methylphenyl)pyrrolidin-3-yl)]urea;
N-(4-Fluorophenyl)-N'-[((R)-1-(3-methylphenyl)pyrrolidin-3-yl)]urea;
N-(4-Fluorophenyl)-N'-[((R)-1-(3-fluorophenyl)]pyrrolidin-3-yl)]urea;
N-(2-Bromophenyl)-N'-[((R)-1-(3-fluorophenyl)pyrrolidin-3-yl)]urea;
N-(1-Naphthyl)-N'-[((R)-1-(3-methylphenyl)pyrrolidin-3-yl)]urea;
N-(2,3-Dichlorophenyl)-N'-[((R)-1-(3-methylphenyl)pyrrolidin-3-yl)]urea;
N-(2-Bromophenyl)-N'-[((S)-1-(3-fluorophenyl)pyrrolidin-3-yl)]urea;
N-(2-Bromophenyl)-N'-[((R)-1-(4-fluoro-3-methylphenyl)pyrrolidin-3-yl)]urea;
N-(2-Bromophenyl)-N'-[((R)-1-(3,4-difluorophenyl)pyrrolidin-3-yl)]urea;
N-(2-Bromophenyl)-N'-[((R)-1-(3-fluoro-4-methylphenyl)pyrrolidin-3-yl)]urea;
N-(3-Chloro-2-methylphenyl)-N'-[((R)-1-(3-methylphenyl)pyrrolidin-3-yl)]urea;
N-(2,3-Dichlorophenyl)-N'-[((R)-1-(3-methylphenyl)pyrrolidin-3-yl)]urea;
N-(2,5-Dichlorophenyl)-N'-[((R)-1-(3-methylphenyl)pyrrolidin-3-yl)]urea;
N-(2,3-Dichlorophenyl)-N'-[((R)-1-(3-fluorophenyl)pyrrolidin-3-yl)]urea;
N-(2,5-Dichlorophenyl)-N'-[((R)-(3-fluorophenyl)pyrrolidin-3-yl)]urea;
N-(3-Chloro-2-methylphenyl)-N'-[((R)-1-(3-fluorophenyl)pyrrolidin-3-yl)]urea;
N-(3-Chloro-2-methylphenyl)-N'-[((R)-1-(3,4-difluorophenyl)pyrrolidin-3-yl)]urea;
N-(2,3-Dichlorophenyl)-N'-[((R)-1-(3,4-difluorophenyl)pyrrolidin-3-yl)]urea;
N-(2,5-Dichlorophenyl)-N'-[((R)-1-(3,4-difluorophenyl)pyrrolidin-3-yl)]urea;
N-(3-Chloro-2-methylphenyl)-N'-[((R)-1-(3-fluoro-4-methylphenyl)pyrrolidin-3-yl)]urea; and
N-(2,3-Dichlorophenyl)-N'-[((R)-1-(3-fluoro-4-methylphenyl)pyrrolidin-3-yl)]urea.

Suitably, P is phenyl, quinolinyl or isoquinolinyl. More suitably P is phenyl, 5-quinolinyl, 7-quinolinyl or 5 isoquinolinyl. Preferably, P is phenyl or 5-isoquinolinyl.
Suitably, P' is phenyl. Suitably, P' is pyridyl.
Suitably, $R^1$ is halo, —CF$_3$ or alkyl. Preferably, $R^1$ is fluoro, chloro, bromo, —CF$_3$, methyl or tert-butyl.
When p is 2 or 3 the groups $R^1$ may be the same or different.
Suitably, p is 1 or 2. Preferably, p is 1.
Suitably, m is 1.
Suitably, n is 0 or 1. Preferably, n is 0.
Suitably, $R^2$ is halo, alkyl, alkoxy, —CN or —CF$_3$. Preferably, $R^2$ is fluoro, chloro, bromo, methyl, OMe or CF$_3$.
Suitably, q is 1 or 2. Preferably, q is 1.
Suitably, x is 1, 2 or 3.
When q is 2 or 3 the groups $R^2$ may be the same or different.

When q is 2, particularly preferred examples of $R^2$ are 3,4-difluoro, 3-fluoro-4-methyl, 3-methyl-4-fluoro, 3-chloro-5-trifluoromethyl, 3-cyano-5-trifluoromethyl and 3-cyano-6-trifluoromethyl.

Suitably, r and s have values such that they define a 4-7 membered ring. Preferably, r and s have values such that they define a 5 or 6 membered ring. Most preferably r and s have values such that they define a 5 membered ring.

According to a further preferred aspect of the present invention, there is provided a subset of compounds of formula (I), of formula (IB),

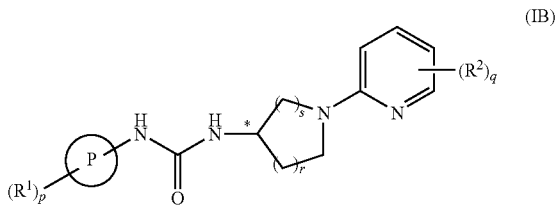

(IB)

or a pharmaceutically acceptable salt thereof, or a solvate thereof, wherein:
P is phenyl, naphthyl, quinolinyl or isoquinolinyl;
$R^1$ and $R^2$ are independently selected from —H, halo, alkyl, alkoxy, cycloalkyl, aralkyl, aralkoxy, cycloalkylalkyl, cycloalkylalkoxy, —CN, —$NO_2$, —OH, —$OCF_3$, —$CF_3$, —$NR^4R^5$, —$S(O)_mR^6$, —$S(O)_2NR^4R^5$, —$OS(O)_2R^6$, —$OS(O)_2CF_3$, —$O(CH_2)_xNR^4R^5$, —$C(O)CF_3$, —C(O)alkyl, —C(O)cycloalkyl, —C(O)aralkyl, —C(O)Ar, —$C(O)(CH_2)_xOR^6$, —$C(O)(CH_2)_xNR^4R^5$, —C(O)alkoxy, —$C(O)NR^4R^5$, —$(CH_2)_xC(O)$alkoxy, —$(CH_2)_xOC(O)R^6$, —$(CH_2)_xOR^6$, —$(CH_2)_xR^4R^5$, —$(CH_2)_xC(O)NR^4R^5$, —$(CH_2)_xN(R^4)C(O)R^6$, —$(CH_2)_xS(O)_2NR^4R^5$, —$(CH_2)_xN(R^4)S(O)_2R^6$, —ZAr, —$(CH_2)_xS(O)_2R^6$, —$(OCH_2)_xS(O)_2R^6$, —$N(R^4)S(O)_2R^6$, —$N(R^4)C(O)R^6$, —$(CH_2)_xN(R^4)S(O)_2R^6$, —$(CH_2)_xN(R^4)C(O)R^6$ or —$(CH_2)_xC(O)$alkyl;
$R^4$ and $R^5$ may be the same or different and represent H or alkyl or $R^4$ and $R^5$ together with the atoms to which they are attached form a $C_{3-6}$azacycloalkane, $C_{3-6}$(2-oxo)azacycloalkane ring or $C_{5-8}$polymethylene chain optionally interrupted by heteroatoms such as O or —$NR^7$.
Z is O, S or $NR^7$;
$R^6$ is alkyl or aryl;
$R^7$ is hydrogen, alkyl or aryl;
m is 1 or 2;
n is 0, 1, 2 or 3;
p and q are independently 0, 1, 2, 3 or 4;
r is 1, 2 or 3;
s is 0, 1 or 2; and
x is 0, 1, 2, 3, 4, 5 or 6.

Suitably, $R^1$ is halo, hydroxy, alkyl, alkoxy, —$CF_3$, —$NO_2$, —CN, —$OCF_3$, amino or mono- or dialkylamino. Preferably, $R^1$ is halo, —$CF_3$ or alkyl. More preferably, $R^1$ is bromo, chloro, fluoro, —$CF_3$, methyl or tert-butyl;

Suitably, $R^1$ is halo, hydroxy, alkyl, alkoxy, —$CF_3$, —$NO_2$, —CN, —$OCF_3$, amino or mono- or dialkylamino. Preferably, $R^2$ is halo, alkyl, alkoxy, —CN, or —$CF_3$. Preferably, $R^2$ is bromo, chloro, fluoro, methyl, —OMe or —$CF_3$;

Suitably, p and q are independently 0, 1 or 2; and
Suitably, r and s are independently 1 or 2.
Suitably, x is 1, 2 or 3.

Compounds of formula (IB) of particular interest according to the present invention are Example numbers 1-23, 28, 29, 34-39, 44-50 and 55-76 (presented in Table 1 below) or pharmaceutically acceptable salts or solvates thereof.

According to a further aspect of the present invention, there is provided a subset of compounds of formula (I), of formula (IC),

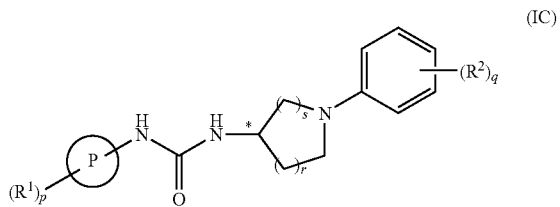

(IC)

or a pharmaceutically acceptable salt thereof, or a solvate thereof, wherein:
P is phenyl, naphthyl, quinolinyl or isoquinolinyl;
$R^1$ and $R^2$ are independently selected from halo, hydroxy, alkyl, alkoxy, —$CF_3$, —$NO_2$, —CN, —$OCF_3$, amino or mono- or dialkylamino
n is 0, 1, 2 or 3;
p and q are independently 0, 1, 2, 3 or 4;
r is 1, 2 or 3; and
s is 0, 1 or 2;
with the proviso that said compound of formula (I) is not a compound selected from:
1-(1-phenyl-3-pyrrolidinyl)-3-phenyl urea;
1-(1-phenyl-3-pyrrolidinyl)-3-(4-methoxyphenyl)urea;
N-(4-Fluorophenyl)-N'-[(R)-1-((3-methylphenyl)pyrrolidin-2-ylmethyl)]urea;
N-(2-Bromophenyl)-N'-[((R)-1-(3-methylphenyl)pyrrolidin-3-yl)]urea;
N-(2-Bromophenyl)-N'-[((R)-1-(3-methylphenyl)pyrrolidin-2-ylmethyl)]urea;
N-(4-Fluorophenyl)-N'-[((S)-1-(3-methylphenyl)pyrrolidin-2-ylmethyl)]urea;
N-(2-Bromophenyl)-N'-[((S)-1-(3-methylphenyl)pyrrolidin-2-ylmethyl)]urea;
N-(4-Fluorophenyl)-N'-[((S)-1-(3-methylphenyl)pyrrolidin-3-yl)]urea;
N-(2-Bromophenyl)-N'-[((S)-1-(3-methylphenyl)pyrrolidin-3-yl)]urea;
N-(4-Fluorophenyl)-N'-[((R)-1-(3-methylphenyl)pyrrolidin-3-yl)]urea;
N-(4-Fluorophenyl)-N'-[((R)-1-(3-fluorophenyl)]pyrrolidin-3-yl)]urea;
N-(2-Bromophenyl)-N'-[((R)-1-(3-fluorophenyl)pyrrolidin-3-yl)]urea;
N-(1-Naphthyl)-N'-[((R)-1-(3-methylphenyl)pyrrolidin-3-yl)]urea;
N-(2,3-Dichlorophenyl)-N'-[((R)-1-(3-methylphenyl)pyrrolidin-3-yl)]urea;
N-(2-Bromophenyl)-N'-[((S)-1-(3-fluorophenyl)pyrrolidin-3-yl)]urea;
N-(2-Bromophenyl)-N'-[((R)-1-(4-fluoro-3-methylphenyl)pyrrolidin-3-yl)]urea;
N-(2-Bromophenyl)-N'-[((R)-1-(3,4-difluorophenyl)pyrrolidin-3-yl)]urea;
N-(2-Bromophenyl)-N'-[((R)-1-(3-fluoro-4-methylphenyl)pyrrolidin-3-yl)]urea;
N-(3-Chloro-2-methylphenyl)-N'-[((R)-1-(3-methylphenyl)pyrrolidin-3-yl)]urea;
N-(2,3-Dichlorophenyl)-N'-[((R)-1-(3-methylphenyl)pyrrolidin-3-yl)]urea;
N-(2,5-Dichlorophenyl)-N'-[((R)-1-(3-methylphenyl)pyrrolidin-3-yl)]urea;

N-(2,3-Dichlorophenyl)-N'-[((R)-1-(3-fluorophenyl)pyrrolidin-3-yl)]urea;
N-(2,5-Dichlorophenyl)-N'-[((R)-1-(3-fluorophenyl)pyrrolidin-3-yl)]urea;
N-(3-Chloro-2-methylphenyl)-N'-[((R)-1-(3-fluorophenyl)pyrrolidin-3-yl)]urea;
N-(3-Chloro-2-methylphenyl)-N'-[((R)-1-(3,4-difluorophenyl)pyrrolidin-3-yl)]urea;
N-(2,3-Dichlorophenyl)-N'-[((R)-1-(3,4-difluorophenyl)pyrrolidin-3-yl)]urea;
N-(2,5-Dichlorophenyl)-N'-[((R)-1-(3,4-difluorophenyl)pyrrolidin-3-yl)]urea;
N-(3-Chloro-2-methylphenyl)-N'-[((R)-1-(3-fluoro-4-methylphenyl)pyrrolidin-3-yl)]urea; and
N-(2,3-Dichlorophenyl)-N'-[((R)-1-(3-fluoro-4-methylphenyl)pyrrolidin-3-yl)]urea.

Suitably, P is phenyl, quinolinyl or isoquinolinyl.
Suitably, $R^1$ is alkyl. Preferably $R^1$ is methyl.
Suitably, $R^2$ is halo or alkyl. Suitably, $R^2$ is fluoro or methyl.
Suitably, p and q are independently 0, 1 or 2.
Suitably, r and s are independently 1 or 2.

Compounds of formula (IC) of particular interest according to the present invention are Example numbers 24-27, 30-33, 40-43 and 51-54 (illustrated in Table 1 below) or pharmaceutically acceptable salts or solvates thereof.

Certain of the carbon atoms of formula (I) are chiral carbon atoms, such as the carbon atom marked with an "*", and therefore compounds of formula (I) may exist as stereoisomers. The invention extends to all optical isomers such as stereoisomeric forms of the compounds of formula (I) including enantiomers and mixtures thereof, such as racemates. The different stereoisomeric forms may be separated or resolved one from the other by conventional methods or any given isomer may be obtained by conventional stereospecific or asymmetric syntheses.

Preferred compounds of formula (I) have the C* carbon in the R-configuration.

Certain of the compounds herein can exist in various tautomeric forms and it is to be understood that the invention encompasses all such tautomeric forms.

As indicated above, the compounds of formula (I) can form salts, especially pharmaceutically acceptable salts. Suitable pharmaceutically acceptable salts are those use conventionally in the art and include those described in *J. Pharm. Sci.*, 1977, 66, 1-19, such as acid addition salts.

Suitable pharmaceutically acceptable salts include acid addition salts.

Suitable pharmaceutically acceptable acid addition salts include salts with inorganic acids such, for example, as hydrochloric acid, hydrobromic acid, orthophosphoric acid or sulphuric acid, or with organic acids such, for example as methanesulphonic acid, toluenesulphonic acid, acetic acid, propionic acid, lactic acid, citric acid, fumaric acid, malic acid, succinic acid, salicylic acid, maleic acid, glycerophosphoric acid or acetylsalicylic acid.

The salts and/or solvates of the compounds of the formula (I) which are not pharmaceutically acceptable may be useful as intermediates in the preparation of pharmaceutically acceptable salts and/or solvates of compounds of formula (I) or the compounds of the formula (I) themselves, and as such form another aspect of the present invention.

The compounds of formula (I) may be prepared in crystalline or non-crystalline form, and if crystalline, may be optionally hydrated or solvated. This invention includes in its scope stoichiometric hydrates as well as compounds containing variable amounts of water.

Suitable solvates include pharmaceutically acceptable solvates, such as hydrates.

Solvates include stoichiometric solvates and non-stoichiometric solvates.

As used herein the term "alkyl" as a group or part of a group refers to a straight or branched chain saturated aliphatic hydrocarbon radical containing 1 to 12 carbon atoms, suitably 1 to 6 carbon atoms. Such alkyl groups in particular include methyl ("Me"), ethyl ("Et"), n-propyl ("Pr$^n$"), iso-propyl ("Pr$^i$"), n-butyl ("Bu$^n$"), sec-butyl ("Bu$^s$"), tert-butyl ("Bu$^t$"), pentyl and hexyl. Where appropriate, such alkyl groups may be substituted by one or more groups selected from halo (such as fluoro, chloro, bromo), —CN, —CF$_3$, —OH, —CF$_3$, $C_{2-6}$ alkenyl, $C_{3-6}$ alkynyl, $C_{1-6}$ alkoxy, aryl and di-$C_{1-6}$ alkylamino.

As used herein, the term "alkoxy" as a group or part of a group refers to an alkyl ether radical, wherein the term "alkyl" is defined above. Such alkoxy groups in particular include methoxy, ethoxy, n-propoxy, iso-propoxy, n-butoxy, isobutoxy, sec-butoxy and tert-butoxy. Where appropriate, such alkoxy groups may be substituted by one or more groups selected from halo (such as fluoro, chloro, bromo), —CN, —CF$_3$, —OH, —OCF$_3$, $C_{1-6}$ alkyl, $C_{2-6}$ alkenyl, $C_{3-6}$ alkynyl, aryl and di-$C_{1-6}$ alkylamino.

As used herein, the term "aryl" as a group or part of a group refers to a carbocyclic aromatic radical ("Ar"). Suitably such aryl groups are 5-6 membered monocyclic groups or 8-10 membered fused bicyclic groups, especially phenyl ("Ph"), biphenyl and naphthyl, particularly naphthyl and phenyl.

As used herein, the term "heteroaryl" as a group or part of a group refers to a stable 5-7-membered monocyclic or 7- to 10-membered bicyclic heterocyclic aromatic ring which consists of carbon atoms and from 1 to 4, suitably from 1 to 2, heteroatoms independently selected from the group consisting of N, O and S. It is preferred that the total number of S and O atoms in the aromatic heterocycle is not more than 1. Examples of suitable heteroaryl groups include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolyl, carbazolyl, carbolinyl, chromanyl, chromenyl, cinnolinyl, decahydroquinolinyl, 2H, 6H-1,5,2-dithiazinyl, dihydrobenzofuranyl, furanyl, furazanyl, imidazolyl, 1H-indazolyl, indolinyl, indolyl, isobenzofuranyl, isochromanyl, isoindazolyl, isoindolyl, isoquinolinyl, isothiazolyl, isoxazolyl, naphthyridinyl, oxadiazolyl, 1,2,3-oxadiazolyl, 1,2,4-oxadiazolyl, 1,2,5-oxadiazolyl, 1,3,4-oxadiazolyl, oxazolyl, pyrimidinyl, phthalazinyl, pteridinyl, purinyl, pyrazinyl, pyrazolyl, pyridooxazolyl, pyridoimidazolyl, pyridothiazolyl, pyridyl, pyrrolyl, quinazolinyl, quinolinyl, quinoxalinyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thiazolyl, thienyl, thienothiazolyl, thienooxazolyl, thienoimidazolyl, triazinyl, 1,2,3-triazolyl, 1,2,4-triazolyl, 1,2,5-triazolyl, 1,3,4-triazolyl and xanthenyl.

The term "halo" is used herein to describe, unless otherwise stated, a group selected from fluorine ("fluoro"), chlorine ("chloro"), bromine ("bromo") or iodine ("iodo").

The term "naphthyl" is used herein to denote, unless otherwise stated, both naphth-1-yl and naphth-2-yl groups.

The present invention also provides a process for the preparation of a compound of formula (I) or a pharmaceutically acceptable salt thereof, which process comprises coupling a compound of formula (II):

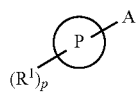
(II)

in which R¹, P and p are as defined in formula (I) with a compound of formula (III):

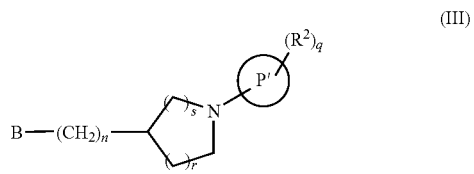
(III)

in which P', R², n, q, r and s are as defined in formula (I) and A and B contain appropriate functional groups which are capable of reacting together to form the urea moiety;

and thereafter, as necessary, carrying out one or more of the following reactions:

(i) converting one compound of formula (I) into another compound of formula (I);

(ii) removing any protecting group;

(iii) preparing a salt or a solvate of the compound so formed.

Suitable examples of appropriate A and B groups include:

(a) A is —N=C=O and B is $NH_2$; or A is $NH_2$ and B is N=C=O or (b) A is $NH_2$ and B is $NH_2$ together with an appropriate urea forming agent.

In process (a) the reaction is carried out in an inert solvent such as dichloromethane or acetonitrile.

In process (b) the urea forming agent can be carbonyl diimidazole or phosgene or triphosgene, and carried out in an inert organic solvent such as diethyl ether, tetrahydrofuran or dichloromethane at ambient or elevated temperature in the presence of a base such as triethylamine or pyridine.

An alternative method of synthesis of the unsymmetrical urea compounds of formula (I) is from a diaryl carbonate, via the corresponding carbamate. Such a methodology is described by Freer et al. (Synthetic Communications, 26(2), 331-349, 1996). It would be appreciated by those skilled in the art that such a methodology could be readily adapted for preparation of the compounds of formula (I).

It will be appreciated by those skilled in the art that it may be necessary to protect certain reactive substituents during some of the above-mentioned procedures. Standard protection and deprotection techniques, such as those described in Greene T. W. 'Protective groups in organic synthesis', New York, Wiley (1981), can be used. For example, primary amines can be protected as phthalimide, benzyl, benzyloxycarbonyl or trityl derivatives. Carboxylic acid groups can be protected as esters. Aldehyde or ketone groups can be protected as acetals, ketals, thioacetals or thioketals. Deprotection of such groups is achieved using conventional procedures well known in the art.

A compound of formula (III) may be prepared by reaction of a compound of formula (IV):

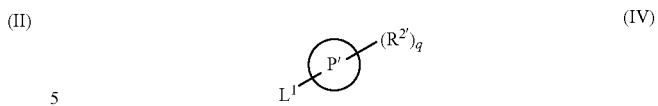
(IV)

wherein, P' is as defined in relation to formula (I) and $R^{2'}$ is $R^2$ as defined above or a protected form thereof, $L^1$ is a leaving group and q is as defined above, with a compound of formula (V):

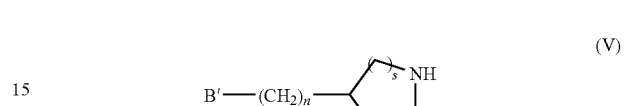
(V)

wherein B' is B as defined above or a protected form thereof and n, r and s are as defined above.

Suitably $L^1$ is a halogen, such as chlorine.

Suitably, the compound of formula (V) is in an activated form, for example an ionic form. Such activated forms are prepared using conventional coupling reaction methodology, as for example by reacting compounds (IV) and (V) in the presence of an alkali carbonate, such as potassium carbonate, in an aprotic solvent such as dimethylformamide using reaction conditions appropriate to the particular methodology chosen, for example at an elevated temperature, such as 100° C.

Compounds of formulae (IV) and (V) are commercially available, or are prepared by known procedures, such as those disclosed in: *Heterocycles,* 1984, 22(1), 117 and J. Chem. Soc., Perkin 1, 1988, 4, 921 for compounds of formula (IV) and *J. Med. Chem.,* 1992, 35(10), 1764 for compounds of formula (V), or by methods analogous to these disclosed methods.

Pharmaceutically acceptable salts may be prepared conventionally by reaction with the appropriate acid or acid derivative.

Compounds of formula (I) and their pharmaceutically acceptable salts have Vanilloid receptor antagonist (VR1) activity and are believed to be of potential use for the treatment or prophylaxis of certain disorders, or treatment of the pain associated with them, such as: pain, chronic pain, neuropathic pain, postoperative pain, postrheumatoid arthritic pain, osteoarthritic pain, back pain, visceral pain, cancer pain, algesia, neuralgia, dental pain, headache, migraine, neuropathies, carpal tunnel syndrome, diabetic neuropathy, HIV-related neuropathy, post-herpetic neuralgia, fibromyalgia, neuritis, sciatica, nerve injury, ischaemia, neurodegeneration, stroke, post stroke pain, multiple sclerosis, respiratory diseases, asthma, cough, COPD, broncho constriction, inflammatory disorders, oesophagitis, heart burn, Barrett's metaplasia, dysphagia, gastroeosophageal relux disorder (GERD), stomach and duodenal ulcers, functional dyspepsia, irritable bowel syndrome, inflammatory bowel disease, colitis, Crohn's disease, pelvic hypersensitivity, pelvic pain, menstrual pain, renal colic, urinary incontinence, cystitis, burns, itch, psoriasis, pruritis, emesis (hereinafter referred to as the "Disorders of the Invention").

Accordingly, the invention also provides a compound of formula (I) or a pharmaceutically acceptable salt or solvate thereof, for use as an active therapeutic substance, in particular in the treatment and/or prophylaxis of the Disorders of the Invention.

In particular, the invention provides a compound of formula (I) or a pharmaceutically acceptable salt or solvate thereof for use in the treatment or prophylaxis of pain.

The invention further provides a method for the treatment or prophylaxis of disorders in which antagonism of the Vanilloid (VR1) receptor is beneficial, in particular the Disorders of the Invention, in mammals including humans, which comprises administering to a mammal in need thereof a therapeutically effective amount of a compound of formula (I) or a pharmaceutically acceptable salt or solvate thereof.

The invention provides for the use of a compound of formula (I) or a pharmaceutically acceptable salt or solvate thereof in the manufacture of a medicament for the treatment or prophylaxis of disorders in which an antagonist of the Vanilloid (VR1) receptor is beneficial, particularly the Disorders of the Invention.

In order to use the compounds of the invention in therapy, they will normally be formulated into a pharmaceutical composition in accordance with standard pharmaceutical practice. Thus, the present invention also provides a pharmaceutical composition, which comprises a compound of formula (I) or a pharmaceutically acceptable salt or solvate thereof and a pharmaceutically acceptable carrier or excipient therefor.

A pharmaceutical composition of the invention, which may be prepared by admixture, suitably at ambient temperature and atmospheric pressure, is usually adapted for oral, parenteral, rectal administration or intravesical administration to the bladder and, as such, may be in the form of tablets, capsules, oral liquid preparations, powders, granules, lozenges, reconstitutable powders, injectable or infusable solutions, suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. For systemic administration, dosage levels from 0.01 mg to 100 mg per kilogramme of body weight are useful in the treatment of pain. However, as a general guide suitable unit doses may be 0.05 to 1000 mg, more suitably 0.05 to 20, 20 to 250, or 0.1 to 500.0 mg, for example 0.2 to 5 and 0.1 to 250 mg; and such unit doses may be administered more than once a day, for example two or three a day, so that the total daily dosage is in the range of about 0.5 to 1000 mg; and such therapy may extend for a number of weeks or months.

No unacceptable toxicological effects are indicated with compounds of the invention when administered in accordance with the invention.

All publications, including but not limited to patents and patent applications, cited in this specification are herein incorporated by reference as if each individual publication were specifically and individually indicated to be incorporated by reference herein as though fully set forth.

The following Descriptions and Examples illustrate the preparation of the compounds of the invention.

Abbreviations
BINAP—2,2'-bis(diphenylphosphino)-1,1'-binaphthyl
HPLC—High Performance Liquid Chromatography
$MgSO_4$—Magnesium sulfate
TFA—Trifluoroacetic acid
DCM—dichloromethane

DESCRIPTION 1

[(R)-1-(5-Trifluoromethylpyridin-2-yl)-pyrrolidin-3-yl]-carbamic acid tert-butyl ester (D1)

To a solution of 2-chloro-5-trifluoromethylpyridine (7.3 g, 0.04 mol) and 3R-(+)-3-(tert-butyloxycarbonylamino)pyrrolidine (7.5 g, 0.04 mol) in dry dimethylformamide (100 ml) was added powdered potassium carbonate (6.6 g, 0.05 mol) and the reaction heated at 100° C. for 7 h and cooled. Solvent was removed under reduced pressure and the residue partitioned between ethyl acetate and water. The organic phase was separated, dried ($MgSO_4$) and filtered. Removal of solvent under reduced pressure gave a solid. Chromatography on silica gel eluting with ethyl acetate and DCM (gradient elution, 20% maximum) afforded the title compound as a white solid.

DESCRIPTION 2

(R)-1-(5-Trifluoromethylpyridin-2-yl)-pyrrolidin-3-ylamine (D2)

A solution of D1 (11.5 g, 0.04 mol) in DCM (80 ml) was cooled (ice-bath) and trifluoroacetic acid (excess, 50 ml) was added. Reaction was warmed to ambient temperature, stirred for 3 h and partitioned between ethyl acetate and aqueous sodium hydroxide. The organic phase was separated, dried ($MgSO_4$) and filtered. Removal of solvent under reduced pressure afforded the crude product as a yellow oil. Bulb to bulb distillation under reduced pressure initially afforded the title compound as an oil which crystallised on standing.

DESCRIPTION 3

1,3-Dimethyl-5-nitroisoquinoline (D3)

1,3-Dimethylisoquinoline [(Chem. Lett., 1983, p. 791), 2.39 g, 15.20 mM], in concentrated sulfuric acid, (15 ml), was cooled to <4° C. A solution of potassium nitrate, (1.69 g, 16.72 mM), in concentrated sulfuric acid was added dropwise, maintaining the temperature below 4° C. After complete addition the solution was stirred at this temperature for a further 2 h then warmed to room temperature for 1 h. The reaction mixture was poured into ice water and the solution basified with sodium hydroxide and extracted with DCM. The extract was washed with brine, dried and concentrated to a yellow solid. Purification by silica gel chromatography afforded the title compound as a yellow crystalline solid.

DESCRIPTION 4

5-Amino-1,3-dimethylisoquinoline (D4)

A solution of D3 (2.01 g, 9.94 mM) and 10% palladium on charcoal (1 g) in methanol was hydrogenated at atmospheric pressure for 1 h. The catalyst was filtered off and the filtrate concentrated under reduced pressure to afford the title compound as an off white solid.

DESCRIPTION 5

3-Methyl-5-nitroisoquinoline (D5)

A solution of 3-methylisoquinoline (5.4 g, 0.038 mol) in concentrated sulfuric acid (30 ml) was cautiously added to a solution of potassium nitrate (4.25 g, 1.1 eq) in concentrated sulfuric acid (23 ml) whilst maintaining the temperature below 4° C. (ice bath). Stirring was continued for 2 h and then temperature raised to ambient. Reaction was further stirred for 3 h and then poured into ice-water slurry (500 ml). Neutralisation using solid potassium carbonate afforded a yellow solid which was filtered and washed with water. The crude product was dissolved in ethanol (200 ml), filtered and concentrated under reduced pressure to afford the title compound as a yellow solid.

DESCRIPTION 6

5-Amino-3-methylisoquinoline (D6)

The title compound was prepared from D5 using the procedure outlined for Description 4.

DESCRIPTION 7

N-(2,2-Dimethoxyethyl)-(1-phenyl)ethylamine (D7)

A solution of α-methylbenzylamine (8.37 g, 0.07 mol) and bromoacetaldehyde dimethylacetal (11.67 g, 0.07 mol) in acetonitrile (150 ml) containing potassium carbonate (12.39 g, 0.09 mol) was heated at reflux for 2d and cooled. The solid was filtered off and the filtrate was concentrated under reduced pressure to leave an oil. Chromatography on silica gel eluting with ethyl acetate afforded the title compound as an oil.

DESCRIPTION 8

1-Methylisoquinoline (D8)

To cooled chlorosulfonic acid (16 ml, −10° C.) was cautiously added D7 (5 g, 0.024 mol) over a period of 2 h. Reaction was allowed to warm to ambient temperature and stirring continued for 3d. The reaction was then poured into ice-water slurry (500 ml), basified using solid potassium carbonate followed by extraction using DCM. Organic phase was separated, dried over MgSO$_4$, filtered and concentrated under reduced pressure to leave an oil. Chromatography on silica gel eluting with ethyl acetate afforded the title compound as yellow oil.

DESCRIPTION 9

1-Methyl-5-nitroisoquinoline (D9)

A solution D8 (1 g, 7 mmol) in sulfuric acid (2.5 ml) was cooled (<4° C.) and concentrated nitric acid (1 ml) added over 10 min. Reaction was stirred for 30 min and then heated at 60° C. for 2 h. After cooling the reaction mixture was poured into ice water slurry (100 ml) and basified using solid potassium carbonate followed by extraction using DCM. Organic phase was separated, dried over MgSO$_4$, filtered and concentrated under reduced pressure to afford the title compound as a white solid.

DESCRIPTION 10

5-Amino-1-methylisoquinoline (D10)

The title compound was prepared from (D9) using the procedure outlined for Description 4.

DESCRIPTION 11

((R)-1-(3-Methylphenyl)pyrrolidin-3-yl)carbamic acid tert-butyl ester (D11)

A suspension of BINAP 1.25 g, 2 mmol), palladium acetate (0.3 g, 1.3 mmol) cesium carbonate (6.6 g, 0.02 mol), 3-bromotoluene (4.6 g, 0.027 mol) and (3R)-(+)-3-(tert-butyloxycarbonylamino)pyrrolidine (2.5 g, 0.013 mol) in 1,4-dioxane (anhydrous, 50 ml) was heated at reflux under an argon atmosphere for 18 h. After cooling, solvent was removed under reduced pressure and residue partitioned between DCM and water. Organic phase was separated, dried over MgSO$_4$, filtered and concentrated under reduced pressure to leave an oil. Chromatography on silica gel eluting with ethyl acetate and hexane (gradient elution, maximum 4%) afforded the title compound as an off-white solid.

DESCRIPTION 12

(R)-1-(3-Methylphenyl)pyrrolidin-3-ylamine (D12)

A solution of D11 (2.07 g, 7.5 mmol) in TFA (1.2 ml) and DCM (20 ml) was stirred at ambient temperature for 18 h. Solvent was removed under reduced pressure and the residue partitioned between DCM and aqueous sodium hydrogen carbonate. Organic phase was separated, dried over MgSO$_4$, filtered and concentrated under reduced pressure to afford the title compound as an oil.

DESCRIPTION 13

(R)-1-(3-Fluorophenylpyrrolidin-3-yl)carbamic acid tert-butyl ester (D13)

The title compound was prepared from (3R)-(+)-3-(tert-butyloxycarbonylamino)pyrrolidine and 1-bromo-3-fluorobenzene using the procedure outlined in Description 11.

DESCRIPTION 14

(R)-1-(3-Fluorophenyl)pyrrolidin-3-ylamine (D14)

The title compound was prepared from D13 using the procedure outlined for Description 12.

DESCRIPTION 15

(R)-1-(3,4-Difluorophenyl)pyrrolidine-3-carbamic acid tert-butyl ester (D15)

The title compound was prepared from (3R)-(+)-3-(tert-butoxycarbonylamino)pyrrolidine and 4-bromo-1,2-difluorobenzene using the procedure outlined for Description 11.

DESCRIPTION 16

(R)-1-(3,4-Difluorophenyl)-pyrrolidin-3-ylamine (D16)

The title compound was prepared from D15 using the procedure outlined for Description 12.

DESCRIPTION 17

(R)-1-(3-Fluoro-4-methylphenyl)pyrrolidine-3-carbamic acid tert-butyl ester (D17)

The title compound was prepared from (3R)(+)-3-(tert-butoxycarbonylamino)pyrrolidine and 4-bromo-2-fluorotoluene using the procedure outlined for Description 11.

DESCRIPTION 18

(R)-1-(3-Fluoro-4-methylphenyl)-pyrrolidin-3-ylamine (D18)

The title compound was prepared from D17 using the procedure outlined for Description 12.

DESCRIPTION 19

(2,2-Diethoxyethyl)-(2-fluorobenzylidene)amine (D19)

2-Fluorobenzaldehyde (7.45 g), was added to aminoacetaldehyde diethylacetal (9.16 g) and the reaction heated to 100° C. for 3 h. After cooling, the mixture was transferred to a separating funnel and partitioned between diethyl ether and water. The ether layer was separated, dried over magnesium sulfate, filtered and concentrated under reduced pressure to leave an oil. Distillation at 0.6-0.8 mm collecting the fraction boiling at 102-106° C. afforded the title compound as a colourless oil.

DESCRIPTION 20

8-Fluoroisoquinoline (D20)

A solution of phosphorus pentoxide, (18 g), in concentrated sulfuric acid, (5 ml), was heated to 160° C. was treated cautiously with a solution of D19 (11.5 g) concentrated sulfuric acid, (75 ml) over a period of 5 mins. After heating for 25 mins the reaction was cooled and poured into ice-water slurry (1 l). Basification with solid sodium hydroxide to pH 10 was followed by extraction with ethyl acetate. The organic phase was dried over magnesium sulfate, filtered and concentrated under reduced pressure to afford the crude product. Chromatography on silica gel eluting with ethyl acetate and hexane (gradient, max 10%) afforded the product as a pale yellow crystalline solid.

DESCRIPTION 21

8-Fluoro-5-nitrolsoquinoline (D21)

D20, (0.278 g), in concentrated sulfuric acid, (2 ml), was cooled to 0° C. Potassium nitrate, (0.21 g), was added portionwise whilst maintaining the temperature below 0° C. After complete addition the solution was stirred at 0° C. for a further 1.5 h and then stirred at ambient temperature for 24 h. The reaction mixture was poured into ice-water slurry, basified with sodium hydroxide and extracted with ethyl acetate. The ethyl acetate solution was dried over magnesium sulfate, filtered and concentrated under reduced pressure to leave the crude product. Purification by silica gel chromatography eluting with ethyl acetate afforded the title compound as a yellow crystalline solid.

DESCRIPTION 22

5-Amino-8-fluoroisoquinoline (D22)

D21, (0.283 g), in ethanol (2 ml), was treated with concentrated hydrochloric acid, (2 ml). Reaction mixture cooled in an ice bath and a solution of tin (II) chloride dihydrate, (1.45 g), in ethanol, (2 ml), was added portionwise over 10 mins. After a further 20 mins the reaction mixture was basified with sodium hydroxide and extracted with DCM. The DCM solution was dried over magnesium sulfate, filtered and concentrated under reduced pressure to leave the crude product. Chromatography on silica gel eluting with ethyl acetate gave the title compound as a cream solid.

DESCRIPTION 23

(1-Benzyl-piperidin-4-yl)-carbamic acid tert-butyl ester (D23)

To a solution of 1-benzyl-4-aminopiperidine (30 g, 0.16 mol) in DCM (200 ml) was added dropwise a solution of di-tert-butyl dicarbonate (1.1 eq., 37.9 g) in DCM (100 ml) over a period of 2 h. Reaction was stirred at ambient temperature for 18 h and then solvent was removed under reduced pressure to afford the title compound as a white solid.

DESCRIPTION 24

Piperidin-4-yl-carbamic acid tert-butyl ester (D24)

A solution of D23 (10 g, 3.4 mmol) in methanol (150 ml) was hydrogenated at 50 psi in a Parr hydrogenator using 10% Palladium on carbon catalyst (800 mg) for 18 h. Catalyst was filtered off and the filtrate concentrated under reduced pressure to afford the title compound as a white solid.

DESCRIPTION 25

1-[((5-Trifluoromethylpyridin-2-yl)piperidin-4-yl) amino]-carbamic acid tert-butyl ester (D25)

The title compound was prepared from D24 and 2-chloro-5trifluoromethylpyridine using the procedure outlined for Description 1.

DESCRIPTION 26

1-(5-Trifluoromethylpyridin-2-yl)piperidin-4-ylamine (D26)

The title compound was prepared from D25 using the procedure outlined for Description 2.

DESCRIPTION 27

3-(3'-isoquinolin-5-yl-ureido)-piperidine-1-carboxylic acid tertbutyl ester (D27)

To a suspension of 1-(tert-butoxycarbonyl)-3-piperidine carboxylic acid (1 g, 4.4 mmol) in toluene (10 ml) and triethylamine (0.68 ml) was added diphenylphosphoryl azide (1.1 eq., 1.33 g). Reaction was heated at reflux for 1 h and cooled. 5-Aminoisoquinoline (629 mg, 4.4 mmol) was added and reaction stirred at ambient temperature for 56 h. Solvent was removed under reduced pressure and the residue chromatographed on silica gel eluting with hexane/ethyl acetate (gradient elution, maximum 50%) to afford the title compound as a foam.

DESCRIPTION 28

N-(Isoquinolin-5-yl)-N'-(piperidin-3-yl)-urea (D28)

The title compound was prepared from D27 using the procedure outlined for Description 2.

DESCRIPTION 29

[(R)-1-(3-Trifluoromethylpyridin-2-yl)-pyrrolidin-3-yl]-carbamic Acid Tert-Butyl Ester (D29)

The title compound was prepared from 2-chloro-3-trifluoromethylpyridine and 3R-(+)-3-(tert-butyloxycarbonylamino)pyrrolidine using the procedure outlined for Description 1.

DESCRIPTION 30

(R)-1-(4-Trifluoromethylpyridin-2-yl)-pyrrolidin-3-ylamine (D30)

The title compound was prepared from D29 using the procedure outlined for Description 2.

DESCRIPTION 31

[(R)-1-(4-Trifluoromethylpyridin-2-yl)-pyrrolidin-3-yl]-carbamic Acid Tert-Butyl Ester (D31)

The title compound was prepared from 2-chloro-4-trifluoromethylpyridine and 3R-(+)-3-(tert-butyloxycarbonylamino)pyrrolidine using the procedure outlined for Description 1.

DESCRIPTION 32

(R)-1-(4-Trifluoromethylpyridin-2-yl)-pyrrolidin-3-ylamine (D32)

The title compound was prepared from D31 using the procedure outlined for Description 2.

DESCRIPTION 33

[(R)-1-(6-Trifluoromethylpyridin-2-yl)-pyrrolidin-3-yl]-carbamic Acid Tert-Butyl Ester (D33)

The title compound was prepared from 2-chloro-6-trifluoromethylpyridine and 3R-(+)-3-(tert-butyloxycarbonylamino)pyrrolidine using the procedure outlined for Description 1.

DESCRIPTION 34

(R)-1-6-Trifluoromethylpyridin-2-yl)-pyrrolidin-3-ylamine (D34)

The title compound was prepared from D33 using the procedure outlined for Description 2.

DESCRIPTION 35

[(R)-1-(3-Chloropyridin-2-yl)-pyrrolidin-3-yl]-carbamic acid tert-butyl ester (D35)

The title compound was prepared from 2,3-dichloropyridine and 3R-(+)-3-(tert-butyloxycarbonylamino)pyrrolidine using the procedure outlined for Description 1.

DESCRIPTION 36

(R)-1-(3-Chloropyridin-2-yl)-pyrrolidin-3-ylamine (D36)

The title compound was prepared from D35 using the procedure outlined for Description 2.

DESCRIPTION 37

[(R)-1-(5-Chloropyridin-2-yl)-pyrrolidin-3-yl]-carbamic acid tert-butyl ester (D37)

The title compound was prepared from 2,5-dichloropyridine and 3R-(+)-3-(tert-butyloxycarbonylamino)pyrrolidine using the procedure outlined for Description 1.

DESCRIPTION 38

(R)-1-(5-Chloropyridin-2-yl)-pyrrolidin-3-ylamine (D38)

The title compound was prepared from D37 using the procedure outlined for Description 2

DESCRIPTION 39

[(R)-1-(5-Bromopyridin-2-yl)-pyrrolidin-3-yl]-carbamic acid tert-butyl ester (D39)

The title compound was prepared from 2-chloro-5-bromopyridine and 3R-(+)-3-(tert-butyloxycarbonylamino)pyrrolidine using the procedure outlined for Description 1.

DESCRIPTION 40

(R)-1 (5-Bromopyridin-2-yl)-pyrrolidin-3-ylamine (D40)

The title compound was prepared from D39 using the procedure outlined for Description 2.

DESCRIPTION 41

[(R)-1-(6-Methylpyridin-2-yl)-pyrrolidin-3-yl]-carbamic acid tert-butyl ester (D41)

The title compound was prepared from 2-chloro-6-methylpyridine and 3R-(+)-3-(tert-butyloxycarbonylamino)pyrrolidine using the procedure outlined for Description 1.

DESCRIPTION 42

(R)-1-(6-Methylpyridin-2-yl)-pyrrolidin-3-ylamine (D42)

The title compound was prepared from D41 using the procedure outlined for Description 2

DESCRIPTION 43

1-[((3-Trifluoromethylpyridin-2-yl)piperidin-4-yl)amino]-carbamic acid tert-butyl ester (D43)

The title compound was prepared from D24 and 2-chloro-3-trifluoromethylpyridine using the procedure outlined for Description 1.

DESCRIPTION 44

1-(3-Trifluoromethylpyridin-2-yl)-piperidine-4-ylamine (D44)

The title compound was prepared from D43 using the procedure outlined for Description 2.

DESCRIPTION 45

1-[((6-Trifluoromethylpyridin-2-yl)piperidin-4-yl)amino]-carbamic acid tert-butyl ester (D45)

The title compound was prepared from D24 and 2-chloro-6-trifluoromethylpyridine using the procedure outlined for Description 1.

DESCRIPTION 46

1-(6-Trifluoromethylpyridin-2-yl)-piperidin-4-ylamine (D46)

The title compound was prepared from D45 using the procedure outlined for Description 2.

DESCRIPTION 47

1-[((4-Trifluoromethylpyridin-2-yl)piperidin-4-yl)amino]-carbamic acid tert-butyl ester (D47)

The title compound was prepared from D24 and 2-chloro-4-trifluoromethylpyridine using the procedure outlined for Description 1.

DESCRIPTION 48

1-(4-Trifluoromethylpyridin-2-yl)-piperidin-4-ylamine (D48)

The title compound was prepared from D47 using the procedure outlined for Description 2.

DESCRIPTION 49

1-[((3-Chloro-5-trifluoromethylpyridin-2-yl)piperidin-4-yl)amino]-carbamic acid tert-butyl ester (D49)

The title compound was prepared from D24 and 2,3-dichloro-5-trifluoromethylpyridine using the procedure outlined for Description 1.

DESCRIPTION 50

1-(3-Chloro-5-trifluoromethylpyridin-2-yl)-piperidin-4-ylamine (D50)

The title compound was prepared from D49 using the procedure outlined for Description 2.

The following amines were prepared using methods to those described above.

(R)-1-(3-Methylpyridin-2-yl)-pyrrolidin-3-ylamine (D51).
(R)-1-(4-Methylpyridin-2-yl)-pyrrolidin-3-ylamine (D52).
(R)-1-(5-Methylpyridin-2-yl)-pyrrolidin-3-ylamine (D53).
(R)-1-(6-Methoxypyridin-2-yl)-pyrrolidin-3-ylamine (D54).
1-(3-Cyano-5-trifluoromethylpyridin-2-yl)-piperidin-4-ylamine (D55).

(3R)-(+)-3-(tert-butyloxycarbonylamino)pyrrolidine, 5-aminoisoquinoline, 1-aminoisoquinoline, 5-aminoquinoline and 7-aminoquinoline are available commercially from TCI (Japan), Aldrich Chemical Company and Specs and BioSpecs B.V. respectively. Di-tert-butyl tricarbonate was prepared according to the procedure outlined in the literature (Org. Synth., 1978, 57, p. 45). 2-methyl-7-aminoquinoline was prepared according to the procedure outlined in the literature (J. Med. Chem., 1977, 20(11), p. 1528).

EXAMPLE 1

N-(2-Bromophenyl)-N'-[((R)-1-(5-trifluoromethyl-2-pyridyl)pyrrolidin-3-yl)]urea (E1)

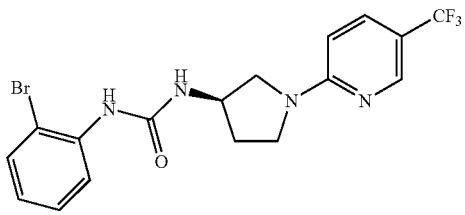

A solution of 2-bromophenyl isocyanate (Aldrich Chemical Company) (27.4 ml, 0.222 mol) in dry diethyl ether (65 ml) was added dropwise over 0.5 h to an efficiently stirred solution of D2 (51.4 g, 0.222 mol) in dry diethyl ether (0.8 L) under argon at ambient temperature. After stirring for 18 h, a white precipitate was filtered off and washed with dry diethyl ether (2×150 ml). The solid was crushed to a fine powder and then re-stirred with diethyl ether (470 ml) for 4 h at ambient temperature. The insoluble product was filtered off, washed with diethyl ether (100 ml) and dried at 50° C./vacuum/24 h to afford title compound as a white solid.

$^1$H NMR (d$_6$-DMSO, 400 MHz) δ 1.94-1.98 (1H, m), 2.19-2.28 (1H, m), 3.31-3.41 (1H, m), 3.56 (2H, br, s), 3.67-3.71 (1H, m), 4.34-4.36 (1H, m), 6.62 (1H, d, J 9.0 Hz), 6.89 (1H, t, J 7.8 Hz), 7.28 (1H, t, J 8.5 Hz), 7.47 (1H, d, J 6.7 Hz), 7.55 (1H, dd, J 8.0, 1.4 Hz), 7.76-7.79 (2H, m), 8.12 (1H, dd, J 8.3, 1.4 Hz), 8.41 (1H, s). MH$^+$ 429, 431.

EXAMPLE 2

N-(Isoquinol-5-yl)-N'-[((R)-1-(5-trifluoromethyl-2-pyridyl)pyrrolidin-3-yl)]urea (E2)

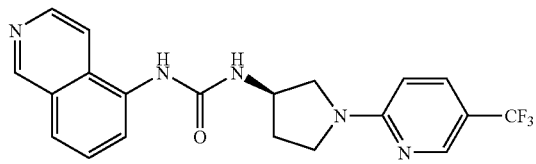

To a solution of di-tert-butyl tricarbonate, (0.681 g, 2.595 mmol), in dry DCM (1 ml) was added a solution of D2, (0.5 g, 2.162 mmol) in dry DCM (1 ml) in one portion. After the initial effervescence, the solution was stirred at room temperature for 0.3 h. A solution of 5-aminoisoquinoline, (0.312 g, 2.162 mmol) in dry DCM (1 ml) was added. The reaction mixture was stirred at room temperature overnight. The resultant precipitate was removed by centrifugation, and the solid washed with ether and dried to give the title compound as a white solid.

$^1$H NMR (d$_6$-DMSO, 250 MHz) δ 9.26 (1H, s), 8.57 (1H, s), 8.52 (1H, d), 8.41 (1H, s), 8.31 (1H, d), 7.88 (1H, d), 7.78 (1H, dd), 7.70 (1H, d), 7.60 (1H, t), 6.99 (1H, d), 6.64 (1H, d), 4.41 (1H, m), 3.73 (1H, dd), 3.59 (2H, m), 3.42 (1H, m), 2.28 (1H, m) and 2.02 (1H, m). MH$^+$ 402

EXAMPLE 3

(±)-N-(Isoquinol-5-yl)-N'-[(1-(5-trifluoromethyl-2-pyridyl)piperidin-3-yl)]urea (E3)

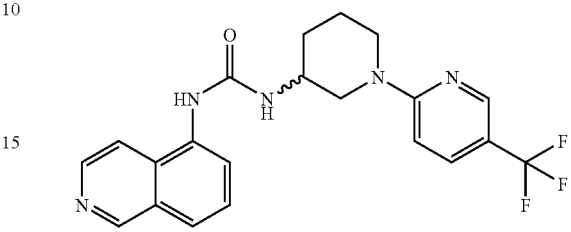

D28 (0.2 g, 0.74 mmol), 2-chloro-5-trifluoromethylpyridine (3 eq., 0.4 g) in dimethylformamide (10 ml) and finely powdered potassium carbonate (3 eq. 0.31 g) were heated at 90° C. for 18 h and cooled. Solvent was removed under reduced pressure and the residue partitioned between ethyl acetate and water. The organic phase was separated, dried (MgSO$_4$) and filtered. Removal of solvent under reduced pressure afforded the crude product. This was chromatographed on silica gel eluting with ethyl acetate to give the title compound as an off-white solid which was converted into a hydrochloride salt. MH$^+$ (free base) 416.

The two enantiomers (E3A and E3B) were separated by HPLC using Chiralpak AD column (250×19 mm id), and eluting with n-hexane:ethanol (80:20 v/v) at a flow rate of 1 ml/min with UV detection at 215 nm.

Examples presented in Table 1 were prepared in accordance with the procedures described herein and similar to those of E1 to E3.

TABLE 1

TABLE 1-continued (I)

| Ex | (R¹)ₚ—P— | S'Chem | s | r | —P'(R²)_q | MH+ |
|---|---|---|---|---|---|---|
| 6 | 2-Br-phenyl | R | 1 | 1 | 6-CF₃-pyridin-2-yl | 429, 431 |
| 7 | 2-Br-phenyl | R | 1 | 1 | 3-Cl-2-methylpyridin-6-yl | 396, 398 |
| 8 | 2-Br-phenyl | R | 1 | 1 | 5-Cl-6-methylpyridin-2-yl | 396, 398 |
| 9 | 2-Br-phenyl | R | 1 | 1 | 5-Br-6-methylpyridin-2-yl | 440, 442 |
| 10 | 2-I-phenyl | R | 1 | 1 | 5-CF₃-6-methylpyridin-2-yl | 477 |
| 11 | 2-Cl-phenyl | R | 1 | 1 | 5-CF₃-6-methylpyridin-2-yl | 385, 387 |
| 12 | 4-tert-butylphenyl | R | 1 | 1 | 3-CF₃-2-methylpyridin-6-yl | 407 |
| 13 | 4-tert-butylphenyl | R | 1 | 1 | 3-Cl-2-methylpyridin-6-yl | 373, 375 |

TABLE 1-continued (I)

| Ex | (R¹)ₚ—P | S'Chem | s | r | P'—(R²)q | MH+ |
|----|---------|--------|---|---|----------|-----|
| 14 | 4-tert-butylphenyl | R | 1 | 1 | 3-Me, 2-Me pyridine | 353 |
| 15 | 4-tert-butylphenyl | R | 1 | 1 | 6-OMe pyridin-2-yl | 369 |
| 16 | 3-CF₃-phenyl | R | 1 | 1 | 5-Cl, 2-Me pyridine | 384, 386 |
| 17 | 2-Cl, 4-CF₃-phenyl | R | 1 | 1 | 5-CF₃, 2-Me pyridine | 452, 454 |
| 18 | 2-Cl, 4-CF₃-phenyl | R | 1 | 1 | 4-CF₃, 2-Me pyridine | 452, 454 |
| 19 | 2-Cl, 4-CF₃-phenyl | R | 1 | 1 | 5-Cl, 2-Me pyridine | 420, 422 |
| 20 | 5-methylquinolin-yl | R | 1 | 1 | 5-CF₃, 2-Me pyridine | 402 |

TABLE 1-continued (I)

| Ex | (R¹)ₚ—P— | S'Chem | s | r | —P'—(R²)_q | MH+ |
|---|---|---|---|---|---|---|
| 21 | 1-methylisoquinolin-(yl) | R | 1 | 1 | 6-methyl-3-CF₃-pyridinyl | 402 |
| 22 | 5-methylisoquinolin-(yl) | R | 1 | 1 | 6-methyl-2-CF₃-pyridinyl | 402 |
| 23 | 5-methylisoquinolin-(yl) | R | 1 | 1 | 6-methyl-3-Cl-pyridinyl | 368, 370 |
| 24 | 5-methylisoquinolin-(yl) | R | 1 | 1 | 3-Me-phenyl | 347 |
| 25 | 5-methylisoquinolin-(yl) | R | 1 | 1 | 3-F-phenyl | 351 |
| 26 | 5-methylisoquinolin-(yl) | R | 1 | 1 | 4-Me-3-F-phenyl | 365 |
| 27 | 5-methylisoquinolin-(yl) | R | 1 | 1 | 3,4-diF-phenyl | 369 |
| 28 | 1-Me-5-methylisoquinolin-(yl) | R | 1 | 1 | 6-methyl-3-CF₃-pyridinyl | 416 |

TABLE 1-continued

| Ex | (R¹)ₚ–P | S'Chem | s | r | P'–(R²)q | MH+ |
|---|---|---|---|---|---|---|
| 29 | 1-Me-isoquinolin-5-yl | R | 1 | 1 | 5-Cl-6-Me-pyridin-3-yl | 380, 382 |
| 30 | 1-Me-isoquinolin-5-yl | R | 1 | 1 | 3-Me-phenyl | 361 |
| 31 | 1-Me-isoquinolin-5-yl | R | 1 | 1 | 3-F-phenyl | 365 |
| 32 | 1-Me-isoquinolin-5-yl | R | 1 | 1 | 3,4-diF-phenyl | 383 |
| 33 | 1-Me-isoquinolin-5-yl | R | 1 | 1 | 3-F-4-Me-phenyl | 379 |
| 34 | 3-Me-isoquinolin-5-yl | R | 1 | 1 | 3-CF₃-2-Me-pyridin-5-yl | 416 |
| 35 | 3-Me-isoquinolin-5-yl | R | 1 | 1 | 4-CF₃-6-Me-pyridin-2-yl | 416 |

TABLE 1-continued (I) Structure: (R¹)ₚ–P–NH–C(=O)–NH–*CH–(pyrrolidine with s and r)–N–P'–(R²)_q

| Ex | (R¹)ₚ–P | S'Chem | s | r | P'–(R²)_q | MH+ |
|---|---|---|---|---|---|---|
| 36 | 5-Me-3-Me-isoquinolin-yl | R | 1 | 1 | 6-Me-3-CF₃-pyridin-2-yl | 416 |
| 37 | 5-Me-3-Me-isoquinolin-yl | R | 1 | 1 | 6-Me-2-CF₃-pyridin-yl | 416 |
| 38 | 5-Me-3-Me-isoquinolin-yl | R | 1 | 1 | 3-Cl-2-Me-pyridinyl | 381, 383 |
| 39 | 5-Me-3-Me-isoquinolin-yl | R | 1 | 1 | 5-Cl-6-Me-pyridin-yl | 380, 382 |
| 40 | 5-Me-3-Me-isoquinolin-yl | R | 1 | 1 | 3-Me-phenyl | 361 |
| 41 | 5-Me-3-Me-isoquinolin-yl | R | 1 | 1 | 3-F-phenyl | 365 |
| 42 | 5-Me-3-Me-isoquinolin-yl | R | 1 | 1 | 3,4-diF-phenyl | 382 |
| 43 | 5-Me-3-Me-isoquinolin-yl | R | 1 | 1 | 2-Me-5-F-phenyl | 379 |

TABLE 1-continued (I)

| Ex | (R¹)ₚ―P― | S'Chem | s | r | ―P'(R²)_q | MH+ |
|---|---|---|---|---|---|---|
| 44 | 3-Me-isoquinolin-5-yl | R | 1 | 1 | 2,6-dimethylpyridin-3-yl | 362 |
| 45 | 3-Me-isoquinolin-5-yl | R | 1 | 1 | 2-Me, 3-Me-pyridinyl | 362 |
| 46 | 3-Me-isoquinolin-5-yl | R | 1 | 1 | 2-Me, 4-Me-pyridinyl | 362 |
| 47 | 3-Me-isoquinolin-5-yl | R | 1 | 1 | 2-Me, 5-Me-pyridinyl | 362 |
| 48 | 3-Me-isoquinolin-5-yl | R | 1 | 1 | 2-Me, 6-OMe-pyridinyl | 378 |
| 49 | 1,3-diMe-isoquinolin-5-yl | R | 1 | 1 | 2-Me, 5-CF₃-pyridinyl | 430 |
| 50 | 1,3-diMe-isoquinolin-5-yl | R | 1 | 1 | 2-Me, 5-Cl-pyridinyl | 396, 398 |

TABLE 1-continued (I)

| Ex | (R¹)ₚ—P— | S'Chem | s | r | —P'—(R²)_q | MH+ |
|---|---|---|---|---|---|---|
| 51 | 1,3-dimethylisoquinolin-5-yl (Me at 1, Me at 3, attached at 5) | R | 1 | 1 | 3,5-dimethylphenyl | 375 |
| 52 | 1,3-dimethylisoquinolin-5-yl | R | 1 | 1 | 3-fluorophenyl | 379 |
| 53 | 1,3-dimethylisoquinolin-5-yl | R | 1 | 1 | 3,4-difluorophenyl | 397 |
| 54 | 1,3-dimethylisoquinolin-5-yl | R | 1 | 1 | 3-fluoro-4-methylphenyl (Me, F) | 393 |
| 55 | 1,3-dimethylisoquinolin-5-yl | R | 1 | 1 | 3-chloro-2-methylpyridinyl | 395, 397 |
| 56 | 1,3-dimethylisoquinolin-5-yl | R | 1 | 1 | 6-methyl-2-(trifluoromethyl)pyridinyl | 430 |

TABLE 1-continued (I)

| Ex | (R¹)ₚ–P | S'Chem | s | r | P'–(R²)_q | MH+ |
|----|---------|--------|---|---|-----------|-----|
| 57 | 3-Me, 1-Me isoquinolin-5-yl | R | 1 | 1 | 3-CF₃, 2-Me pyridine | 430 |
| 58 | 3-Me, 1-Me isoquinolin-5-yl | R | 1 | 1 | 4-CF₃, 2-Me pyridine | 430 |
| 59 | 8-F isoquinolin-5-yl | R | 1 | 1 | 5-CF₃, 2-Me pyridine | 420 |
| 60 | isoquinolin-5-yl | | 1 | 2 | 5-CF₃, 2-Me pyridine | 416 |
| 61 | isoquinolin-5-yl | | 1 | 2 | 5-CF₃, 2-Me pyridine | 416 |
| 62 | isoquinolin-5-yl | — | 2 | 1 | 3-CF₃, 2-Me pyridine | 416 |
| 63 | isoquinolin-5-yl | — | 2 | 1 | 4-CF₃, 2-Me pyridine | 416 |

TABLE 1-continued (I)

| Ex | (R¹)ₚ—P— | S'Chem | s | r | —P'—(R²)_q | MH+ |
|---|---|---|---|---|---|---|
| 64 | 5-methylisoquinoline | — | 2 | 1 | 2-methyl-5-CF₃-pyridine | 416 |
| 65 | 5-methylisoquinoline | — | 2 | 1 | 6-methyl-2-CF₃-pyridine | 416 |
| 66 | 5-methylquinoline | — | 2 | 1 | 3-CF₃-2-methyl-pyridine | 416 |
| 67 | 5-methylquinoline | — | 2 | 1 | 6-methyl-2-CF₃-pyridine | 416 |
| 68 | 7-methylquinoline | — | 2 | 1 | 3-CF₃-2-methyl-pyridine | 416 |
| 69 | 2,7-dimethylquinoline | — | 2 | 1 | 3-CF₃-2-methyl-pyridine | 430 |
| 70 | 3-methyl-5-methylisoquinoline | — | 2 | 1 | 3-Cl-5-CF₃-2-methyl-pyridine | 463, 465 |
| 71 | 3-methyl-5-methylisoquinoline | — | 2 | 1 | 6-methyl-2-CF₃-pyridine | 430 |

TABLE 1-continued (I)

| Ex | (R¹)ₚ—P | S'Chem | s | r | (R²)_q—P' | MH+ |
|---|---|---|---|---|---|---|
| 72 | Me-isoquinoline (3-Me, attached at 5) | — | 2 | 1 | 3-CN, 2-CF₃-pyridine (with Me) | 455 |
| 74 | Me-isoquinoline (3-Me, attached at 5) | — | 2 | 1 | 4-CF₃, 2-Me-pyridine | 430 |
| 75 | Me-isoquinoline (3-Me, attached at 5) | — | 2 | 1 | 3-CF₃, 2-Me-pyridine | 430 |
| 76 | 2-Br, methylphenyl | S | 1 | 1 | 5-CF₃, 2-Me-pyridine | 429, 431 |
| 77 | Me-cinnoline (3-Me, attached at 5) | R | 1 | 1 | 5-CF₃, 2-Me-pyridine | 417 |

S'Chem = stereochemistry

Pharmacological Data
(a) In Vitro Assay

As referenced above, the compounds of the invention are vanilloid receptor (VR1) antagonists and hence have useful pharmaceutical properties. Vanilloid receptor (VR1) antagonist activity can be confirmed and demonstrated for any particular compound by use of conventional methods, for example those disclosed in standard reference texts such as D. Le Bars, M. Gozarin and S. W. Cadden, Pharmacological Reviews, 2001, 53(4), 597-652] or such other texts mentioned herein.

The screen used for the compounds of this invention was based upon a FLIPR based calcium assay, similar to that described by Smart et al. (British Journal of Pharmacology, 2000, 129, 227-230). Transfected astrocytoma 1321N1 cells, stably expressing human VR1, were seeded into FLIPR plates at 25,000 cells/well (96-well plate) and cultured overnight.

The cells were subsequently loaded in medium containing 4 μM Fluo-3 AM (Molecular Probes) for 2 hours, at room temperature, in the dark. The plates were then washed 4 times with Tyrode containing 1.5 mM calcium, without probenecid. The cells were pre-incubated with compound or buffer control at room temperature for 30 minutes. Capsaicin (Sigma) was then added to the cells. Compounds having antagonist activity against the human VR1 were identified by detecting differences in fluorescence when measured after capsaicin addition, compared with no compound buffer controls. Thus, for example, in the buffer control capsaicin addition results in an increase in intracellular calcium concentration resulting in fluorescence. A compound having antagonist activity blocks the capsaicin binding to the receptor, there is no signalling and therefore no increase in intracellular calcium levels and consequently lower fluorescence. pKb values are generated from the $IC_{50}$ values using the Cheng-Prusoff equation.

All compounds tested by the above methodology had pKb>6, preferred compounds having a pKb>7.0.

(b) FCA-Induced Hyperalgesia in the Guinea Pig

100 μl of 1 mg/ml FCA was injected intraplantar into the left paw of 4 groups of 8 male Dunkin Hartley guinea-pigs (batch: 6282434, average weight 340 g). 24 hours later compounds were administered orally at 0 (vehicle), 3, 10 30 mg/kg with vehicle as 1% methylcellulose and dosing volume being 2 ml/kg and dosing straight into the stomach. The methylcellulose was added gradually to the compound into the pestle and mortar and ground together.

Behavioural readouts of mechanical hyperalgesia were obtained before FCA administration (naïve reading), after FCA but before drug administration (predose reading) and 1 hour after drug administration. The readout used was paw pressure (Randall-Sellito) and the end point was paw withdrawal. The paw pressure equipment also had one silver disc placed on the point to increase the markings by a factor of 2.

Compounds having a pKb>7.0 in vitro, according to model (a) above, were tested in this model and shown to be active.

The invention claimed is:

1. The compound

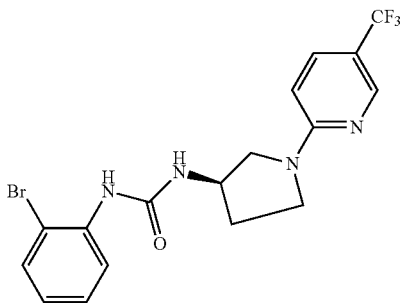

or a pharmaceutically acceptable salt thereof.

2. A pharmaceutical composition comprising a compound according to claim 1.

3. A pharmaceutical composition comprising a salt according to claim 1.

* * * * *

UNITED STATES PATENT AND TRADEMARK OFFICE
CERTIFICATE OF CORRECTION

| | | |
|---|---|---|
| PATENT NO. | : 8,063,078 B2 | Page 1 of 1 |
| APPLICATION NO. | : 10/489277 | |
| DATED | : November 22, 2011 | |
| INVENTOR(S) | : Rami et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1880 days.

Signed and Sealed this
Seventeenth Day of April, 2012

David J. Kappos
*Director of the United States Patent and Trademark Office*